United States Patent
Steele et al.

(10) Patent No.: US 8,828,059 B2
(45) Date of Patent: Sep. 9, 2014

(54) ELONGATED CONNECTING ELEMENTS FOR MINIMALLY INVASIVE SURGICAL PROCEDURES

(75) Inventors: Bradley E. Steele, Germantown, TN (US); Matthew Van Nortwick, Memphis, TN (US); Daniel Paxton Wall, Medina, TN (US); Richard Quinn Brown, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 105 days.

(21) Appl. No.: 13/093,311

(22) Filed: Apr. 25, 2011

(65) Prior Publication Data

US 2012/0271355 A1    Oct. 25, 2012

(51) Int. Cl.
*A61B 17/70* (2006.01)

(52) U.S. Cl.
CPC ......... *A61B 17/7008* (2013.01); *A61B 17/7089* (2013.01); *A61B 17/7031* (2013.01)
USPC .......................................... 606/265; 606/259

(58) Field of Classification Search
CPC ........................ A61B 17/7008; A61B 17/7085
USPC ................................................. 606/246–279
See application file for complete search history.

(56) References Cited

U.S. PATENT DOCUMENTS

| | | | |
|---|---|---|---|
| 4,648,388 A | 3/1987 | Steffee | |
| 4,653,481 A * | 3/1987 | Howland et al. | 606/261 |
| 4,854,304 A | 8/1989 | Zielke | |
| 5,020,519 A | 6/1991 | Hayes | |
| 5,129,388 A | 7/1992 | Vignaud et al. | |
| 5,242,443 A | 9/1993 | Kambin | |
| 5,480,440 A | 1/1996 | Kambin | |
| 5,720,751 A | 2/1998 | Jackson | |
| 5,938,662 A | 8/1999 | Rinner | |
| 6,599,294 B2 | 7/2003 | Fuss et al. | |
| 6,648,888 B1 | 11/2003 | Shluzas | |
| 6,660,006 B2 | 12/2003 | Markworth et al. | |
| 6,682,532 B2 | 1/2004 | Johnson et al. | |
| 6,821,277 B2 | 11/2004 | Teitelbaum et al. | |
| 6,966,910 B2 | 11/2005 | Ritland | |
| 7,108,698 B2 | 9/2006 | Robbins et al. | |
| 7,156,849 B2 | 1/2007 | Dunbar et al. | |
| 7,160,300 B2 | 1/2007 | Jackson | |
| 7,175,622 B2 | 2/2007 | Farris | |
| 7,179,261 B2 | 2/2007 | Sicvol et al. | |
| 7,476,240 B2 * | 1/2009 | Raymond et al. | 606/279 |
| 7,553,320 B2 * | 6/2009 | Molz et al. | 606/247 |
| 7,666,211 B2 * | 2/2010 | Perez-Cruet et al. | 606/250 |
| 7,927,360 B2 * | 4/2011 | Pond et al. | 606/265 |
| 8,012,182 B2 * | 9/2011 | Couedic et al. | 606/264 |

(Continued)

*Primary Examiner* — Ellen C Hammond
(74) *Attorney, Agent, or Firm* — Sorell Lenna & Schmidt LLP (57) ABSTRACT

Apparatus and methods include an elongate connecting element including a body extending along a longitudinal axis between a first end and an opposite second end. The connecting element includes a first end portion at its first end and a second end portion at its second end. The connecting element includes a length between the first and second ends sized to extend between and be engaged to first and second anchors engageable to bony portions of the spinal column. The first and second end portions are positioned on opposite sides of the first and second anchors and project outwardly from the body of the connecting element to capture the first and second anchors between the first and second end portions.

20 Claims, 8 Drawing Sheets

(56) References Cited

U.S. PATENT DOCUMENTS

| | | |
|---|---|---|
| 8,206,395 B2 * | 6/2012 | McLean et al. ............ 606/86 A |
| 8,303,628 B2 * | 11/2012 | Dewey et al. ................ 606/246 |
| 2003/0093078 A1 | 5/2003 | Ritland |
| 2003/0220689 A1 | 11/2003 | Ritland et al. |
| 2003/0225408 A1 | 12/2003 | Nichols et al. |
| 2004/0039384 A1 | 2/2004 | Boehm, Jr. et al. |
| 2004/0049191 A1 | 3/2004 | Markworth et al. |
| 2004/0138662 A1 | 7/2004 | Landry et al. |
| 2004/0143265 A1 | 7/2004 | Landry et al. |
| 2004/0172022 A1 | 9/2004 | Landry et al. |
| 2004/0215190 A1 | 10/2004 | Nguyen et al. |
| 2004/0267275 A1 | 12/2004 | Cournoyer et al. |
| 2005/0010219 A1 | 1/2005 | Dalton |
| 2005/0010221 A1 | 1/2005 | Dalton |
| 2005/0033299 A1 | 2/2005 | Shluzas |
| 2005/0080418 A1 | 4/2005 | Simonson et al. |
| 2005/0085813 A1 | 4/2005 | Spitler et al. |
| 2005/0131405 A1 | 6/2005 | Molz et al. |
| 2005/0131421 A1 | 6/2005 | Anderson et al. |
| 2005/0131422 A1 | 6/2005 | Anderson et al. |
| 2005/0154389 A1 | 7/2005 | Sclover et al. |
| 2005/0182407 A1 | 8/2005 | Dalton |
| 2005/0192589 A1 * | 9/2005 | Raymond et al. ............... 606/99 |
| 2005/0197660 A1 | 9/2005 | Haid et al. |
| 2005/0277931 A1 * | 12/2005 | Sweeney et al. ................ 606/61 |
| 2006/0036260 A1 | 2/2006 | Runco et al. |
| 2006/0079899 A1 | 4/2006 | Ritland |
| 2006/0084993 A1 | 4/2006 | Landry et al. |
| 2006/0106380 A1 | 5/2006 | Colleran et al. |
| 2006/0142761 A1 | 6/2006 | Landry et al. |
| 2006/0173454 A1 | 8/2006 | Spitler et al. |
| 2006/0184178 A1 | 8/2006 | Jackson |
| 2006/0229614 A1 * | 10/2006 | Foley et al. ..................... 606/61 |
| 2006/0241600 A1 * | 10/2006 | Ensign et al. ................... 606/61 |
| 2007/0016188 A1 | 1/2007 | Boehm et al. |
| 2007/0016198 A1 | 1/2007 | Boehm et al. |
| 2007/0016199 A1 | 1/2007 | Boehm et al. |
| 2008/0154308 A1 * | 6/2008 | Sherman et al. .............. 606/265 |
| 2009/0204156 A1 * | 8/2009 | McClintock et al. ......... 606/278 |
| 2009/0275983 A1 * | 11/2009 | Veldman et al. .............. 606/258 |
| 2010/0211107 A1 * | 8/2010 | Muhanna ...................... 606/264 |
| 2011/0022093 A1 | 1/2011 | Sherman et al. |

* cited by examiner

ELONGATED CONNECTING ELEMENTS FOR MINIMALLY INVASIVE SURGICAL PROCEDURES

BACKGROUND

The invention relates generally to medical devices and procedures. More particularly, the invention relates to devices and methods for spinal stabilization.

Stabilization of one or more levels of the spine is often accomplished with placement of an elongated connecting element, such as a rod construct, between bone anchors engaged to the vertebrae of the one or more levels. These procedures may employ various techniques and approaches for positioning the rod into the patient for engagement to the bone anchors. Depending on the technique and surgical instruments that are employed, differing types of rods may be selected for insertion into the patient. For example, rods that are implanted in percutaneous minimally invasive procedures where the rod is guided through skin and tissue to the anchors may employ a configuration that is not optimal for implantation in an open or mini-open surgical procedure in which the rod is positioned minimally invasively or invasively into the patient along a retracted tissue pathway. Furthermore, differing types of rods may be required in order function properly with differing types of insertion instruments or insertion techniques. Therefore, multiple types of rods are required to be available depending on the type of surgical procedure to be employed.

Thus, a need exists for improved elongated connecting elements and procedures for insertion and securement of elongated connecting elements at locations within a patient's body that can be employed in different types of surgical approaches and insertion instruments.

SUMMARY

Apparatus, methods, systems, procedures and implants for stabilization of one or more levels of the spine are described herein. The systems include an elongate connecting element including a body extending along a longitudinal axis between a first end and an opposite second end. The connecting element includes a first end portion at its first end and a second end portion at its second end. The connecting element includes a length between the first and second ends sized to extend between and be engaged to first and second anchors engageable to bony portions of the spinal column. The first and second end portions are positioned on opposite sides of the first and second anchors and project outwardly from the body of the connecting element to capture the first and second anchors between the first and second end portions. The apparatus, methods, systems, procedures and implants minimize invasiveness of the procedure into the patient. Applications in non-minimally invasive procedures are also contemplated.

According to one aspect, an implant system includes at least a first anchor engageable to a first vertebra and a second anchor engageable to a second vertebra. The system further includes an elongate connecting element extending along a longitudinal axis between a first end and an opposite second end with a length between the first and second ends sized to extend between and be engaged to the first and second anchors when the first and second anchors are engaged to the first and second vertebrae. The first and second vertebrae may be adjacent vertebrae, or include one or more vertebrae therebetween. The connecting element includes at least one end portion projecting outwardly from the body to contact at least one of the anchors to prevent the connecting element from passing through the anchor. In one embodiment, the anchor includes an elongated extension extending proximally from a bone engaging portion of the anchor, and the end portion of the connecting element contacts the extension to prevent the connecting element from passing through the extension. In another embodiment, the connecting element includes a second end portion at an opposite end thereof that contacts the other anchor and confines the first and second anchors between the end portions such that the connecting element cannot pass through either of the anchors while allowing the connecting element to be slidably adjusted along the extensions of the anchors.

According to another aspect, an implant system includes at least a first anchor engageable to a first vertebra and a second anchor engageable to a second vertebra. The implant system also includes an elongate connecting element having first and second end portions projecting outwardly therefrom. In a first orientation of the connecting element, the end portions are configured to pass through the first and second anchors. In a second orientation of the connecting element, the end portions contact opposite sides of the anchors to prevent the connecting element from passing through the anchors.

According to yet another aspect, a method comprises inserting into a patient an elongate connecting member between first and second anchors engaged to first and second vertebrae. In one embodiment, the connecting element includes end portions on opposite sides of the anchors that confine the anchors between the end portions as the connecting element is moved distally along the anchors to an implantation location. As used herein, "confine" or "confining" the anchors between the end portions means that the anchors or any portion thereof are located entirely or substantially entirely between the end portions and the end portions prevent the connecting element from passing through opposite side openings of the anchor. In another embodiment, the connecting element is inserted in an endwise manner through the anchors and then rotated from its insertion orientation so the end portions of the connecting element contact opposite sides of the anchors to confine the anchors between the end portions such that the connecting element cannot pass though the anchors when moved in an endwise manner. As used herein, movement or prevention of movement of the connecting element in an "endwise manner" or "endwise approach" means moving the connecting element in a direction defined by the longitudinal axis of the connecting element.

These and other aspects are also discussed below.

DETAILED DESCRIPTION

For the purposes of promoting an understanding of the principles of the invention, reference will now be made to the embodiments illustrated in the drawings and specific language will be used to describe the same. It will nevertheless be understood that no limitation on the scope of the invention is intended. Any alterations and further modifications in the illustrated devices and described methods and further applications of the principles of the invention as disclosed herein are contemplated as would normally occur to one skilled in the art to which the invention relates.

Systems and methods include elongated connecting elements insertable into the body of a patient for stabilization along, for example, two or more vertebrae of a spinal column. The connecting element can be positioned into the patient in minimally invasive surgical approaches where the connecting element is guided through skin and/or tissue of the patient to the implantation location. The connecting element can also be positioned into the patient in minimally invasive, mini-open and open surgical approaches where the skin and/or tissue is at least partially retracted along the insertion path of the connecting element. In one embodiment, the connecting element comprises a portion of a stabilization construct that includes at least two anchors engageable to respective ones of first and second vertebrae and the elongated connecting element is positioned between and engaged to the at least two anchors.

In one embodiment, the connecting element is positioned in a first orientation so that the connecting element can be guided through the anchors in an end-wise manner such that the leading end of the connecting element is initially introduced through a first anchor and then advanced toward and through a second anchor. The connecting element may be introduced directly into its implantation location on the anchors, or through extensions of the anchors that extend proximally from the implantation location through the skin of the patient. The connecting element is then rotated so that the anchors and/or first and second anchor extensions are confined between end portions that project outwardly from the ends of the connecting element. It is also contemplated that the connecting elements can be configured to extend between or be positioned between three or more anchors engaged to three or more vertebrae.

In a further embodiment, the connecting element is initially positioned in an orientation so that end portions of the connecting element capture first and second extensions of first and second anchors between the end portions. The connecting element is guided along the extensions to an implantation location on the anchors while maintaining the confined relationship with the anchors to prevent the connecting element from disengaging or passing through one or both of the extensions as it is moved distally to the implantation location. Other embodiments contemplate connecting elements that extend between or are positioned between three or more anchors engaged to three or more vertebrae.

In addition, a method includes inserting percutaneously or through a small incision at least first and second anchors and engaging the first and second anchors to respective ones of first and second bony portions. The method also includes guiding an elongated connecting element into the patient along a minimally invasive insertion path and between the anchors, and confining the anchor extensions and/or the anchors between outwardly projecting end portions of the connecting element during insertion of the connecting element or after the connecting element is located between the anchors.

In some embodiments, elongate extensions extend proximally from first and second anchors that are engaged to first and second bony portions of vertebrae. An inserter is mounted to a proximal end portion of at least one of the elongate extensions, and an elongate connecting element is guided to the first and second anchors by moving the inserter relative to the at least one extension. In other embodiments, the method includes guiding the elongate connecting element to a location between first and second anchors with an inserter that is not mounted to the anchor extensions. In either embodiment the connecting element is positioned in an insertion orientation so that an outwardly projecting end portion of the connecting element can pass through the extensions and/or anchors in an endwise manner. In either embodiment, the connecting element can be engaged to the anchors in its insertion orientation, or the connecting element can be rotated about its longitudinal axis to confine the anchors between outwardly projecting end portions of the connecting element before the connecting element is finally secured to the anchors.

Figure 1:
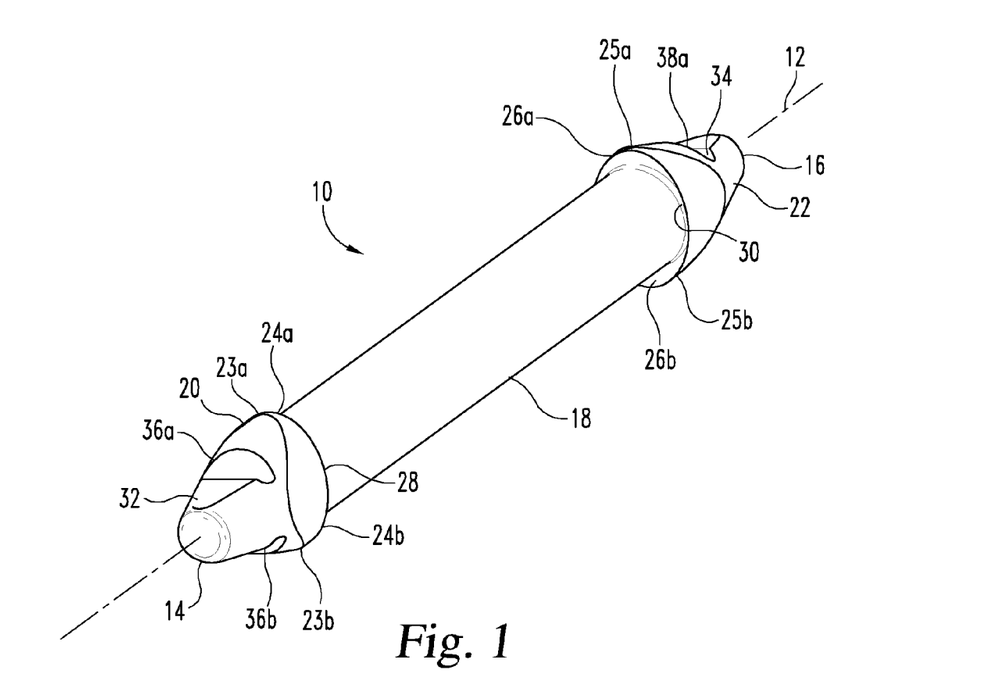
FIG. 1 is a perspective view of one embodiment elongate connecting element.

In FIG. 1 there is shown an elongate connecting element 10 extending along a longitudinal axis 12 between a first end 14 and an opposite second end 16. Connecting element 10 includes a body 18 lying on longitudinal axis 12. In the illustrated embodiment, body 18 includes a circular cross-section orthogonal to longitudinal axis 12, although non-circular cross-sections are also contemplated. Connecting element 10 also includes a first end portion 20 at first end 14 and a second end portion 22 at said end 16. End portion 20 includes opposite flanges 23a, 23b that project outwardly adjacent to first end 14 to form first and second lips 24a, 24b. End portion 22 includes opposite flanges 25a, 25b that project outwardly from body 18 adjacent to second end 16 to form lips 26a, 26b. In the illustrated embodiment, lips 24a, 24b and lips 26a, 26b do not extend completely around body 18. Rather, lips 24a, 24b and lips 26a, 26b project outwardly only at diametrically opposite sides of body 18 so that end portions 20, 22 include an oval or oval-like cross-sectional shape orthogonal to longitudinal axis 12. End portions 20, 22 are aligned with one another so that lips 24a, 26a project outwardly from the same side of body 18, and lips 24b, 26b project outwardly from the same side of body 18 that is directly opposite the side of lips 24a, 26a. The intermediate sides 28, 30 (and their respective directly opposite sides not shown) of end portions 20, 22 include a substantially smaller lip, or do not include a flange or outwardly projecting lip but provide a smooth profile formed by an extension of the cross-section of body 18 along the intermediate sides 28, 30 of end portions 20, 22. Thus, end portions 20, 22 each have a cross-section dimension at sides 28, 30 that is less than the cross-sectional dimension defined by lips 24, 26. End portions 20, 22 also each include a tapered end portion 32, 34 extending to the respective end 14, 16. End portions 20, 22 further each include at least one recess or notch 36a, 38a in at least one side thereof for engagement to an inserter instrument, as discussed below. It is contemplated that a pair of identical notches 36a, 36b can be provided in the opposite sides of end member 20 and also in end member 22 (only notch 38a shown).

Figure 2:
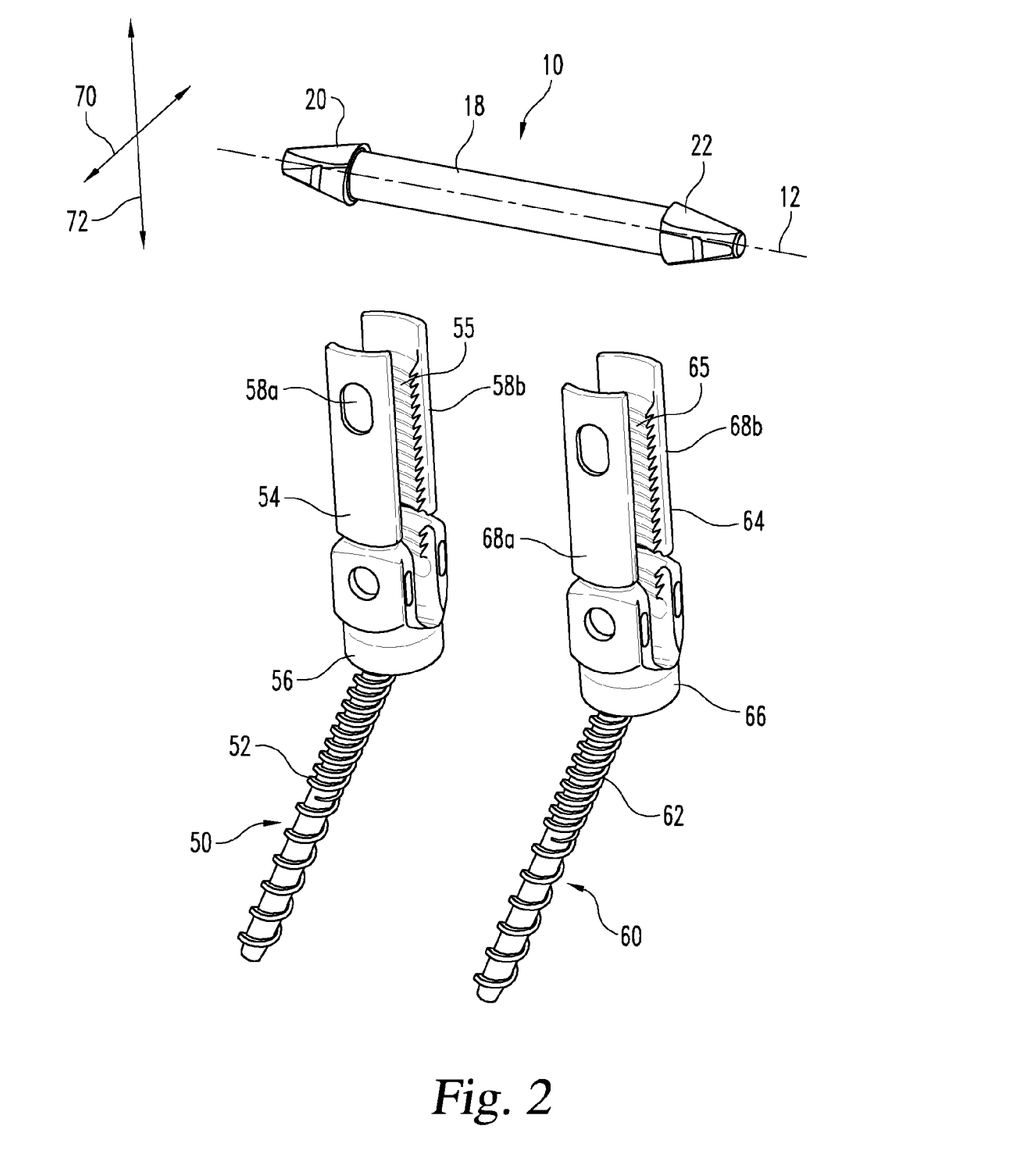
FIG. 2 a perspective view of the connecting element of FIG. 1 and a pair of anchors with extensions for receiving the connecting element from a proximal approach.

Referring now to FIG. 2, there is shown a stabilization system 45 that includes a first anchor 50 and a second anchor 60 spaced from one another. In the illustrated embodiment, anchors 50, 60 each include a bone engaging portion 52, 62 and an extender 54, 64 coupled to the bone engaging portion. Extenders 54, 64 each include a receiving portion 56, 66 adjacent to the respective bone engaging portion that defines a support surface to receive connecting element 10 in its implantation location. Extenders 54, 64 also include removable extension portions 58a, 58b and 68a, 68b, respectively, extending from the corresponding receiving portion 56, 66. Extension portions 58a, 58b and 68a, 68b are sized to extend proximally from the bone engaging portion to a location outside the patient to provide a path to receiving portion 56, 66 in the patient. Further details of one example of suitable anchors with removable extension portions are provided in U.S. Patent App. Pub. No. 2007/0191840 published on Aug. 16, 2007, which is incorporated herein by reference in its entirety. Other embodiments contemplate a suitable anchor and extender extending from the anchor for use in system 45, including anchors that do not include removable extension portions.

Figure 3:
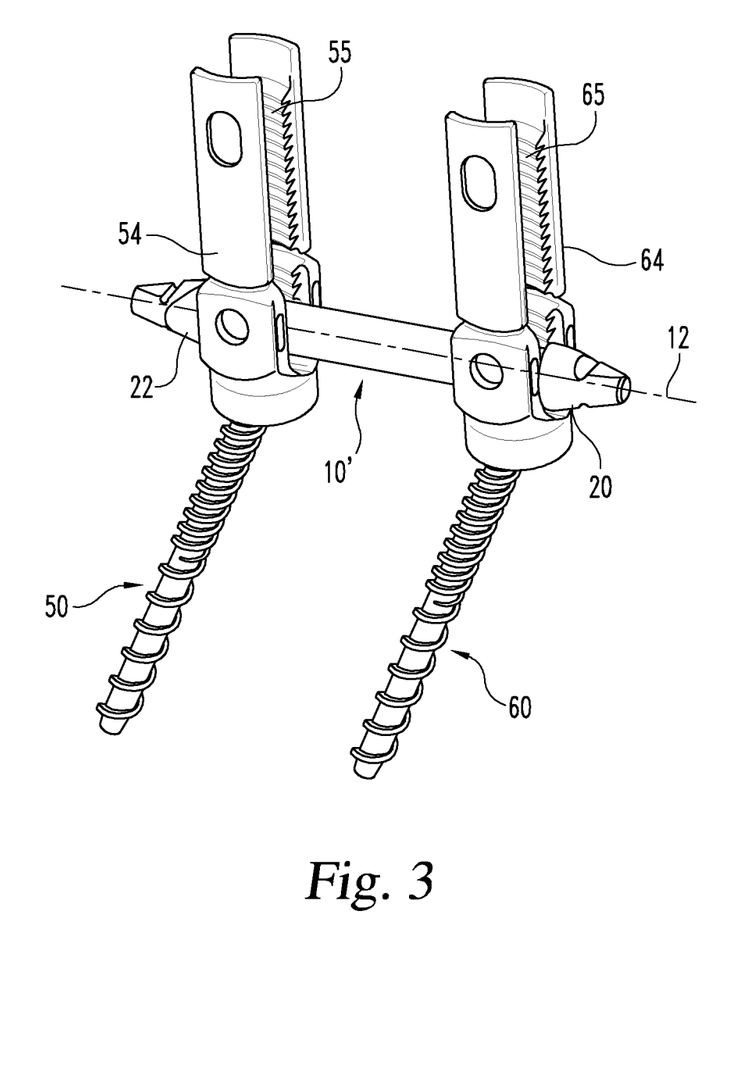
FIG. 3 is a perspective view of the connecting element and anchor assemblies of FIG. 2 with the connecting element positioned in the anchor assemblies.

Connecting element 10 is shown in FIG. 2 located outside the proximal ends of extenders 54, 64 and positioned with end portions 20, 22 oriented laterally, as indicated by arrowed line 70. Connecting element 10 is then positioned in this orientation through the proximal end openings of extenders 54, 64 so that extenders 54, 64 are confined between end portions 20, 22. The outwardly projecting end portions 20, 22 are sized so that they cannot pass through the spaces 55, 65 defined between break-off portions 58a, 58b of extender 54 and break-off portions 68a, 68b of extender 64 in the insertion orientation. End portions 20, 22 prevent connecting element 10 from slipping out of extenders 54, 64 as it is guided along extenders 54, 64 in a distal direction toward receiving portions 56, 66, as indicated by the down arrow of arrowed line 72. In addition, it is contemplated that end portions 20, 22 are sized to project outwardly from receiving portions 56, 66 of anchors 50, 60 to prevent connecting element 10 slipping out of anchors 50, 60 when implanted to the position shown in FIG. 3. Once connecting element 10 is positioned in receiving portions 56, 66, connecting element 10 can be maintained in its insertion orientation, or rotated a quarter turn about longitudinal axis 12 as shown by connecting element 10' in FIG. 3. In either orientation, connecting element 10, 10' can be secured in receiving portions 56, 66 with an engaging member, such as a set screw, cap nut or other suitable member engageable to anchors 50, 60.

Figure 4:
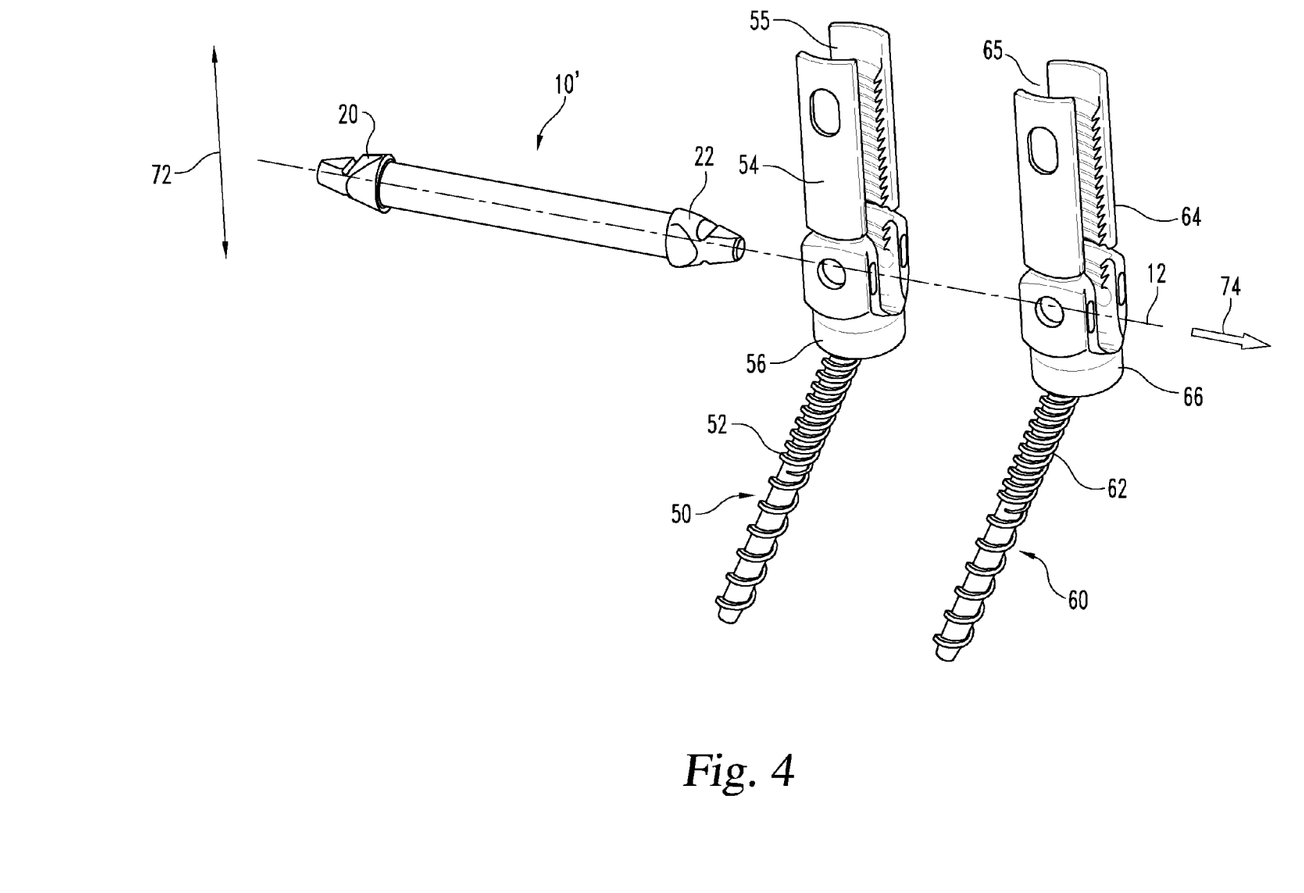
FIG. 4 a perspective view of the connecting element of FIG. 1 and a pair of anchor assemblies with extensions for receiving the connecting element from an endwise approach.
Figure 5:
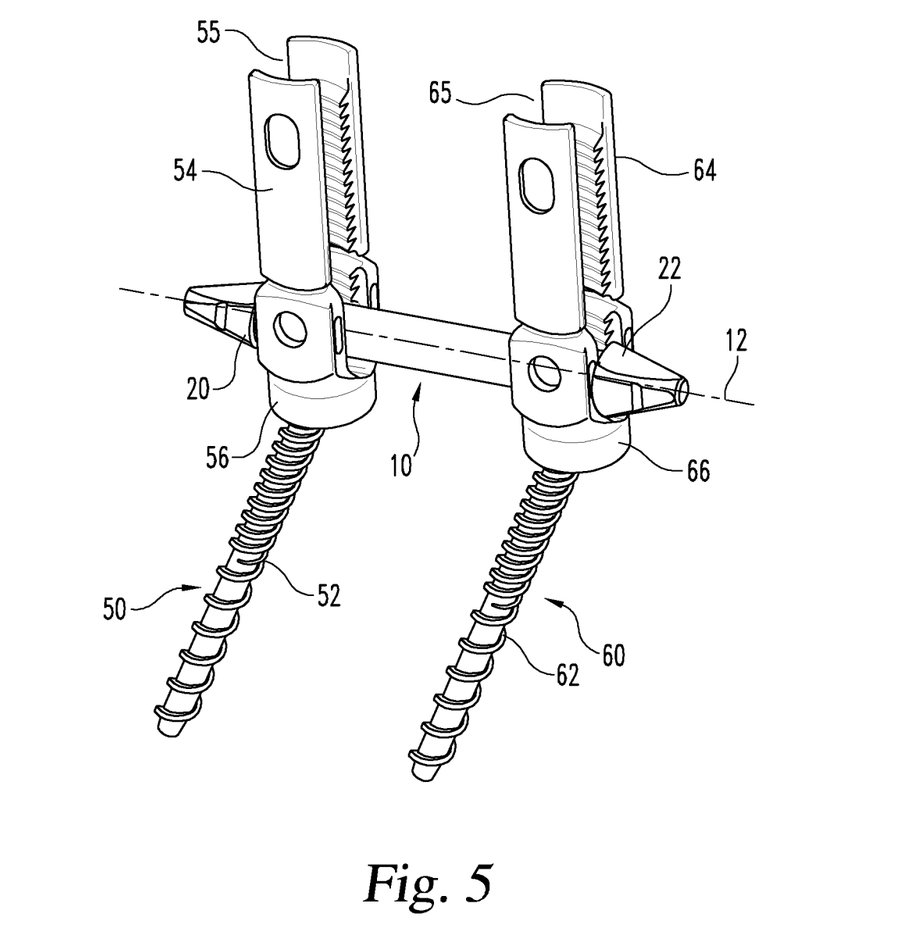
FIG. 5 is a perspective view of the connecting element and anchor assemblies of FIG. 4 with the connecting element positioned in the anchor assemblies from the endwise approach.

Connecting element 10 can also be guided in an end-wise orientation or manner through extenders 54, 64 and/or receiving portions 56, 66. Connecting element 10' is shown in FIG. 4 located outside the receiving portion 56 of anchor 50. In this orientation, end portions 20, 22 extend in the distal and proximal directions as indicated by arrowed line 72. Connecting element 10' is then advanced in this orientation to pass end portion 22 through space 55 of anchor 50 and space 65 of anchor 60, as indicated by arrow 74 and as shown in FIG. 5. End portion 20 does not pass into and remains outside of anchor 50. Connecting element 10' can then be secured to anchors 50, 60 in this insertion orientation, or rotated a quarter turn about longitudinal axis 12 as shown in FIG. 5 and to confine receiving portions 56, 66 between end portions 20, 22 and secured to anchors 50, 60 in the rotated orientation, as shown by connecting element 10 in FIG. 5. In other embodiments, connecting element 10' can be positioned through spaces 55, 65 along extensions 54, 64 and then reduced distally into receiving portions 56, 66 to the implantation location.

Figure 6:
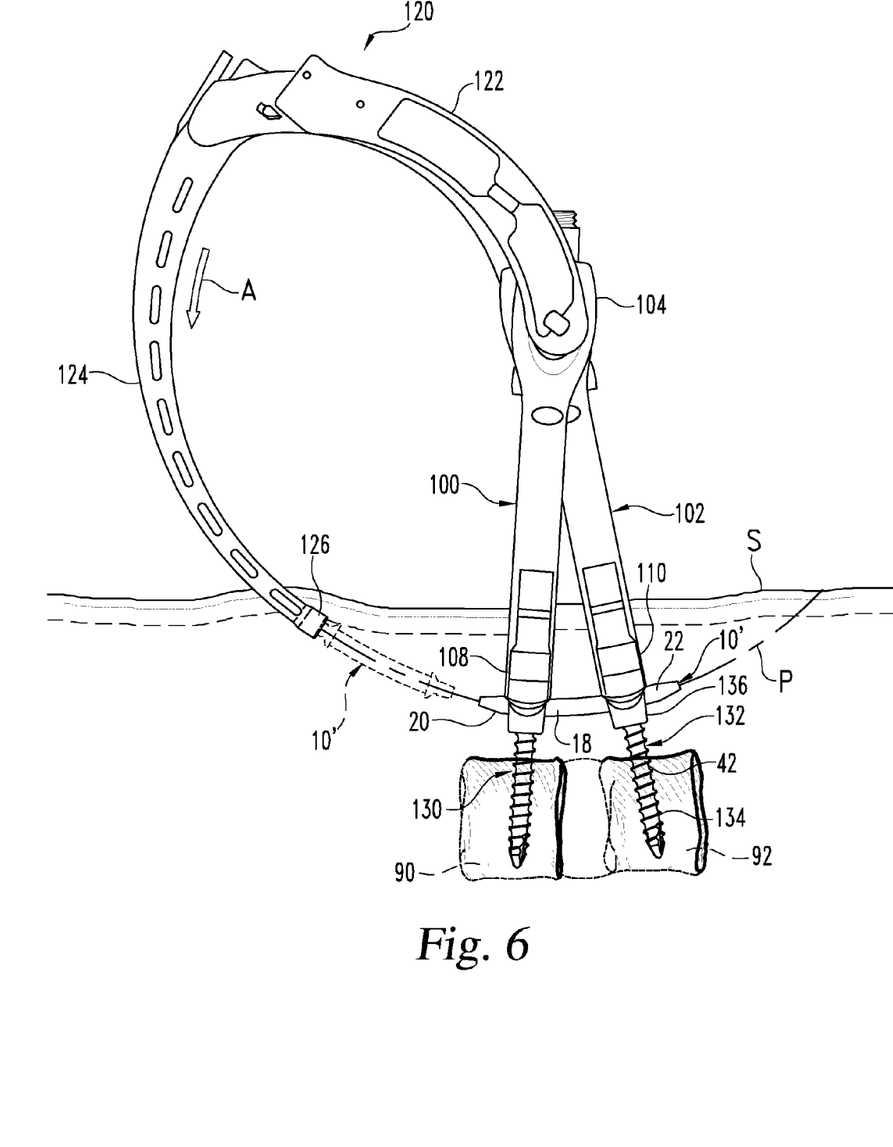
FIG. 6 is an elevational view of an inserter instrument and connecting element engaged thereto for positioning the connecting element to anchors engaged to a diagrammatically shown spinal motion segment.
Figure 7:
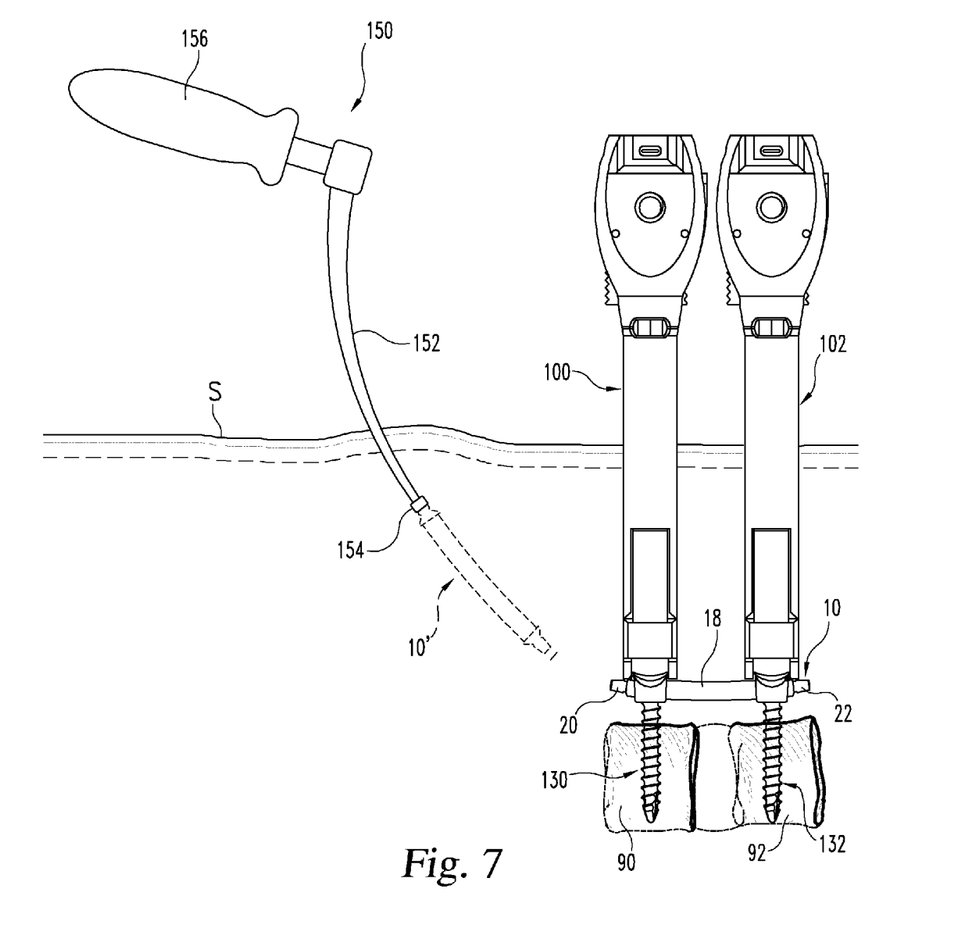
FIG. 7 an elevational view of another embodiment inserter instrument and connecting element engaged there for positioning the connecting element to anchors engaged to a diagrammatically shown spinal motion segment.

FIGS. 6-7 show other embodiments insertion technique and instrumentation for implanting the connecting element 10. In FIGS. 6-7, vertebrae 90, 92 are shown diagrammatically and positioned below skin level S with tissue of the patient between the vertebrae and skin S. It is contemplated that the spinal column segment is part of a patient in which spinal surgery is to be performed with the present invention. It is also contemplated that the spinal column segment may comprise a non-human or non-living animal substrate, such as may be present with a training model to teach methods employing the surgical instruments and implants discussed herein.

Anchors 130, 132 are engaged to vertebrae 90, 92. Anchors 130, 132 each include a bone engaging portion 134 and a receiving portion 136 mounted to bone engaging portion 134. In the illustrated embodiment, bone engaging portion 134 is a bone screw and receiving portion 136 is a saddle or U-shaped head pivotally mounted to the head of the bone screw. Bone engaging portions 134 are shown as bone screws, but can also include any suitable bone engagement structure, including hooks, staples, spikes, bolts, wires, or clamps, for example. Receiving portion 136 is movable to rotate around the head of the bone screw to align passages of the receiving portions 136 to receive connecting element 10, 10' in either orientation depending on the insertion technique that is employed. The passages of receiving portions 136 open proximally to receive a set screw, cap or other engaging member to secure connecting element 10 in receiving portions 136. Other embodiments contemplate receiving portions with laterally opening or obliquely opening passages, or passages that are encircled by receiving portion 136. In any event, the receiving portions 136 open at the cephaladly and caudally oriented sides of receiving portions 136 to accept connecting element 10' in an endwise manner from an insertion path P so that a leading end of connecting element 10' passes through anchor 130 and then anchor 132 and an opposite trailing end of connecting element 10' is located adjacent to anchor 130.

The insertion instrumentation includes anchor extensions 100, 102 extending proximally from respective ones of anchors 130, 132 through skin level S to proximal end portions 104, 106. Extensions 100, 102 include distal end portions 108, 110, respectively, removably engaged to the receiving portions of respective ones of anchors 130, 132. The insertion instrumentation further includes an inserter 120 mounted to proximal end portions 104, 106 of extensions 100, 102. Inserter 120 includes a mounting portion 122 movably mounted to extensions 100, 102, and an elongate arm 124 extending transversely from mounting portion 122 for movement along an arc A that parallels insertion path P. Connecting element 10' is removably engageable to the distal end 126 of elongate arm 124 in an insertion orientation where end portions 20, 22 are oriented proximally and distally so that end portion 22 can pass through opposite side openings of anchors 130, 132 without interference. Connecting element 10' is movable with inserter 120 along insertion path P through skin S and tissue of the patient from a location outside the patient toward anchors 130, 132 and then between anchors 130, 132 for engagement thereto. Additional features and embodiments of anchor extensions and inserters are provided in U.S. Pat. No. 6,530,929 issued Mar. 11, 2003; U.S. Pat. No. 7,188,626 issued Mar. 13, 2007; U.S. Patent App. Pub. No.

2005/0171540 published on Aug. 4, 2005; U.S. Patent App. Pub. No. 2007/0049931 published on Mar. 1, 2007; and U.S. Patent App. Pub. No. 2008/0319477 published on Dec. 5, 2008; each of which is incorporated herein by reference in its entirety.

FIG. 7 shows a second inserter 150 positioned through an incision in skin S to guide connecting element 10' in an endwise manner through anchors 130, 132. Inserter 150 includes an arm 152 with a distal end 154 engaged to end portion 20 of connecting element 10' and a proximal handle 156. Inserter 150 is employed to guide connecting element 10' to anchors 130, 132 in a freehand technique. The surgeon can monitor insertion and positioning of fusion implant 50 using fluoroscopy or other suitable imaging system. Additional details and embodiments of second inserter 150 are disclosed in U.S. Pat. No. 7,520,879 issued Apr. 21, 2009, which is incorporated herein by reference in its entirety.

Figure 8:
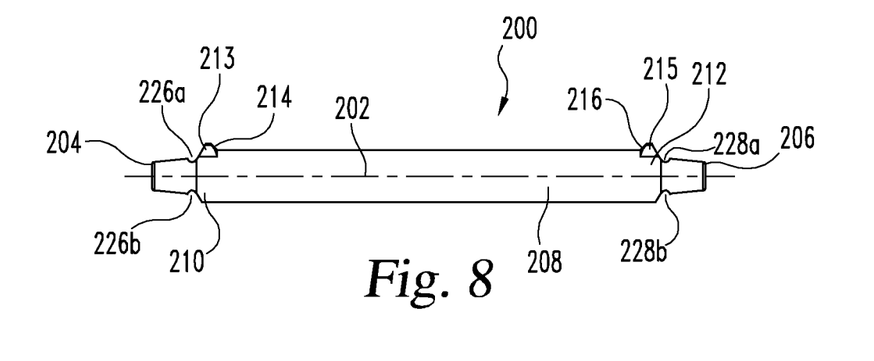
FIG. 8 is a side elevation view of another embodiment connecting element.
Figure 9:
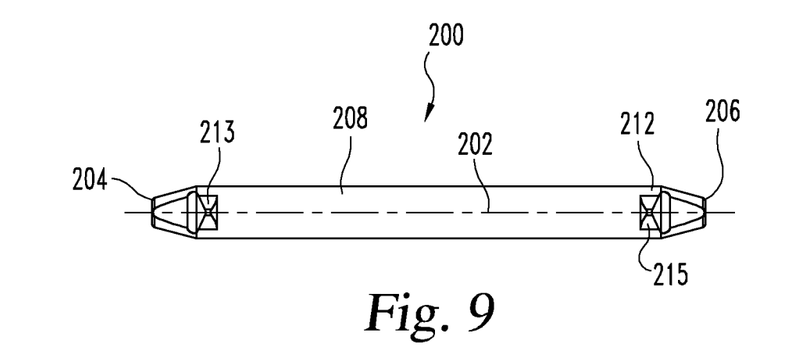
FIG. 9 is a plan view of the connecting element of FIG. 8.
Figure 10:
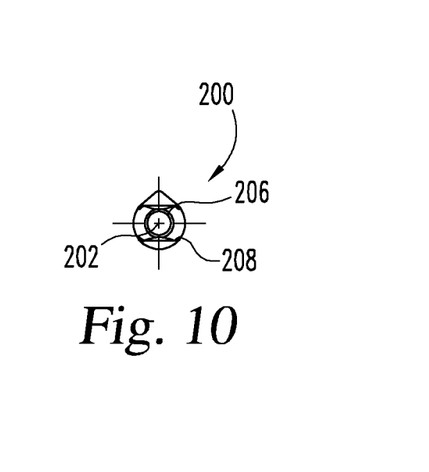
FIG. 10 is an end elevation view of the connecting element of FIG. 8.

FIGS. 8-10 show another embodiment connecting element 200. Connecting element 200 extends along a longitudinal axis 202 between a first end 204 and an opposite second end 206. Connecting element 200 includes a body 208 lying on longitudinal axis 202. In the illustrated embodiment, body 208 includes a circular cross-section orthogonal to longitudinal axis 202, although non-circular cross-sections are also contemplated. Connecting element 200 also includes a first end portion 210 at first end 204 and a second end portion 212 at second end 206. End portions 210, 212 each include a flange 213, 215 projecting outwardly from body 208 to form lips 214, 216, respectively. In the illustrated embodiment, lips 214, 216 do not extend completely around body 208. Rather, lips 214, 216 project outwardly only at one side of body 208. End portions 210, 212 are aligned with one another so that lips 214, 216 project outwardly from the same side of body 18. The remaining sides of end portions 210, 212 do not include an outwardly projecting flange but provide a smooth profile forming a tapered extension of the cross-section of body 208. End portions 210, 212 further each include at least one recess or notch 226a, 226b and notches 228a, 228b, respectively, in at least one side thereof for engagement to an inserter instrument, as discussed above. In this embodiment, connecting element 200 can be inserted in an endwise manner through anchors in close contact with supporting surfaces of the anchors at the implantation location one the anchors without having to offset the connecting element proximally from the support surface to accommodate flanges located on the distal side of the connecting element 200, such as is present with connecting element 10 discussed above. In any event, connecting element 200 is insertable for engagement to any of the anchors discussed herein using any of the instruments, techniques, and procedures discussed herein.

It is contemplated that the connecting element can be comprised of a metal material, such as stainless steel, titanium, chrome-cobalt alloys. The connecting element may also be comprised of a polymer, such as, for example, polyetheretherketone (PEEK), polyetherketoneketone (PEKK), polymethylmethacrylate, polyurethane, silicone, silicone-polyurethane copolymers, epoxy, polycarbonate, polyketone, polyester, polyethylene, polyimide, polylactic acid, polypropylene, polystyrene, polysulfone, polyvinyl chloride, polyamide, poly(tetrafluoroethene), polyphthalamide, polybutylene and mixtures or combinations of thereof. In addition, the connecting element can be linear along its longitudinal axis, curved along its longitudinal axis so that its longitudinal axis and body define an arc having at least one radius, or comprise multiple curved and/or linear segments along its length. In addition, the connecting element can be rigid to completely prevent spinal motion when secured to the anchors, semi-rigid to allow at least limited position, or flexible to permit motion between predefined limits of extension and/or flexion.

Although various embodiments have been described as having particular features and/or combinations of components, other embodiments are possible having a combination of any features and/or components from any of embodiments as discussed above. As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the terms "proximal" and "distal" refer to the direction closer to and away from, respectively, an operator (e.g., surgeon, physician, nurse, technician, etc.) who would insert the medical implant and/or instruments into the patient. For example, the portion of a medical instrument first inserted inside the patient's body would be the distal portion, while the opposite portion of the medical device (e.g., the portion of the medical device closest to the operator) would be the proximal portion.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the invention as defined herein or by any of the following claims are desired to be protected.

What is claimed is:
1. An implant system, comprising:
at least a first anchor engageable to a first vertebra and a second anchor engageable to a second vertebra, said first and second anchors each including an inner surface defining an implant cavity; and
an elongate connecting element disposed in said implant cavities such that an outer surface of said connecting element engages the inner surfaces of said first and second anchors, said connecting element including a body extending along a longitudinal axis between a first end and an opposite second end, wherein said body has a circular cross section defining a uniform width, said connecting element comprising a first end portion at said first end and a second end portion at said second end, said connecting element including a length between said first and second ends disposed in said implant cavities with said first and second end portions positioned on opposite sides of said first and second anchors, said first and second end portions each projecting outwardly from said body and having a maximum width that is greater than the width of said body and maximum widths of said implant cavities to confine said first and second anchors between said first and second end portions such that the connecting element is prevented from moving relative to the anchors along the longitudinal axis in a first direction and a second direction that is opposite the first direction,
wherein said connecting element is rotatable around said longitudinal axis from a first orientation where said first and second anchors are confined between said first and second end portions to a second orientation wherein said end portions are oriented to pass through said first and second anchors.
2. The system of claim 1, wherein said connecting element is rigid to prevent motion of the first and second vertebrae when engaged to the first and second vertebrae with said first and second anchors.

3. The system of claim 2, wherein each of said end portions includes at least one notch for engagement by an inserter instrument.

4. The system of claim 1, wherein each of said end portions of said connecting element includes an oval cross-sectional shape orthogonal to said longitudinal axis.

5. The system of claim 1, wherein each of said end portions is tapered toward a respective one of said first and second ends.

6. The system of claim 1, wherein each of said end portions includes first and second flanges projecting outwardly from said body to form first and second lips at opposite sides of said body.

7. The system of claim 1, wherein each of said end portions includes a single flange projecting from no more than one side of said body.

8. The system of claim 1, wherein said body is linear along said longitudinal axis.

9. The system of claim 1, wherein said body is curved along said longitudinal axis.

10. The system of claim 1, wherein said implant cavities extend between a planar first end surface and a planar second end surface and interfaces between said body and said first and second end portions define a planar lip, at least one end surface of each anchor engaging one of said lips.

11. The system of claim 1, wherein said connecting element is monolithic and has a fixed maximum length.

12. The system of claim 1, wherein:
each of said end portions includes first and second flanges projecting outwardly from said body to form first and second lips at opposite sides of said body; and
each of said end portions has a smooth, arcuate profile between said first and second flanges.

13. The system of claim 1, wherein:
each of said end portions includes first and second flanges projecting outwardly from said body to form first and second lips at opposite sides of said body;
the implant cavities each have a maximum length defined by a distance between opposite end surfaces of a respective one of said first and second anchors; and
the first and second flanges of said first end portion engage one of said end surfaces of said first anchor and the first and second flanges of said second end portion engage one of said end surfaces of said second anchor.

14. An implant system, comprising:
at least a first anchor engageable to a first vertebra and a second anchor engageable to a second vertebra, said first and second anchors each including a bone engaging portion extending distally, a receiver coupled to said bone engaging portion comprising an inner surface defining an implant cavity and an elongated extension extending proximally from said receiver, said extensions each defining a passage therethrough that opens at opposite sides of said extension; and
an elongate connecting element disposed in said implant cavities such that an outer surface of said connecting element engages the inner surfaces of said first and second anchors, said connecting element including a body extending along a longitudinal axis between a first end and an opposite second end, said body having a circular cross section defining a uniform width, said connecting element further including a first end portion at said first end projecting outwardly from said body and a second end portion at said second end projecting outwardly from said body, said first and second end portions each having a maximum width that is greater than the width of said body and maximum widths of said passages such that said connecting element has a first orientation wherein said first and second end portions are spaced apart from said first and second anchors and a second orientation wherein said first and second end portions contact opposite sides of said extensions to prevent the connecting element from moving relative to the anchors along the longitudinal axis in a first direction and a second direction that is opposite the first direction while allowing said connecting element to move proximally and distally along said extensions;
wherein said connecting element is rotatable around said longitudinal axis from the first orientation to the second orientation.

15. The system of claim 14, wherein opposite first and second sides of said connecting element each include an outwardly projecting flange and opposite third and fourth sides of said connecting member each have a smooth, arcuate profile such that said connecting element is rotated a quarter-turn around said longitudinal axis to move said connecting element between said first and second orientations.

16. The system of claim 14, wherein each of said end portions of said connecting element includes an oval cross-sectional shape orthogonal to said longitudinal axis.

17. The system of claim 16, wherein each of said end portions is tapered toward a respective one of said first and second ends.

18. The system of claim 17, wherein each of said end portions includes at least one notch for engagement by an inserter instrument.

19. The system of claim 14, wherein each of said end portions includes first and second flanges projecting outwardly from said body to form first and second lips at opposite sides of said body.

20. The system of claim 14, wherein each of said end portions includes a single flange projecting from no more than one side of said body.

* * * * *